United States Patent [19]

Baacke et al.

[11] Patent Number: 4,721,609

[45] Date of Patent: Jan. 26, 1988

[54] PROCESS FOR PREPARING A PENTASIL ZEOLITE

[75] Inventors: Michael Baacke; Peter Kleinschmit, both of Hanau, Fed. Rep. of Germany

[73] Assignee: Degussa Aktiengesellschaft, Frankfurt, Fed. Rep. of Germany

[21] Appl. No.: 903,625

[22] Filed: Sep. 2, 1986

[30] Foreign Application Priority Data

Sep. 13, 1985 [DE] Fed. Rep. of Germany ....... 3532748

[51] Int. Cl.$^4$ ............................................. C01B 33/28
[52] U.S. Cl. .................................. 423/329; 423/328; 502/60; 502/77
[58] Field of Search .................. 423/328, 329; 502/60, 502/77; 564/292, 295

[56] References Cited

U.S. PATENT DOCUMENTS

| | | | |
|---|---|---|---|
| 4,481,174 | 11/1984 | Baacke et al. | 502/77 |
| 4,481,177 | 11/1984 | Valyocsik | 502/77 |
| 4,531,012 | 7/1985 | Valyocsik | 502/77 |
| 4,537,754 | 8/1985 | Casci et al. | 423/277 |
| 4,557,919 | 12/1985 | Sumitani et al. | 502/77 |
| 4,568,654 | 2/1986 | Valyocsik | 502/62 |
| 4,585,638 | 4/1986 | Kuhl | 423/328 |
| 4,585,639 | 4/1986 | Szostak | 423/328 |

FOREIGN PATENT DOCUMENTS 0065401 11/1982 European Pat. Off. ............ 423/328

OTHER PUBLICATIONS

Robert Thornton Morrison and Robert Neilson Boyd, *Organic Chemistry*, Allyn and Bacon Inc., Boston, (1973).

Morrison and Boyd, *Organic Chemistry*, 3rd Edition, Allyn and Bacon Inc., Boston, (1973), pp. 452–475, 738, 740, 752–753.

*Primary Examiner*—William R. Dixon, Jr.
*Assistant Examiner*—Jackson Leeds

*Attorney, Agent, or Firm*—Beveridge, DeGrandi & Weilacher

[57] ABSTRACT

Templating compounds of the formula:

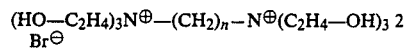

wherein n equals 3, 4 or 5 are produced by reacting triethanolamine with α, ωdibromoalkanes, for example in the presence of a solvent. One can also react dibromoalkane with the triethanolamine in dropwise manner at reaction temperature. The product is subsequently recovered by known methods. The templating compositions can be used for the preparation of the zeolites of the pentasil types. These zeolites have the composition represented by the summary formula:

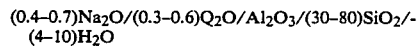

and have the following X-ray diffraction pattern:

| d Å | I/Io |
|---|---|
| 11.0 ± 0.2 | 30–70 |
| 10.0 ± 0.2 | 30–80 |
| 4.4 ± 0.1 | 10–20 |
| 4.3 ± 0.1 | 10–20 |
| 3.85 ± 0.05 | 100 |
| 3.74 ± 0.05 | 40–65 |
| 3.66 ± 0.05 | 20–40 |
| 3.43 ± 0.03 | 15–25 |
| 2.01 ± 0.02 | 5–15 |
| 1.99 ± 0.02 | 5–15 |

They are prepared by utilizing an aqueous suspension of precipitated silica and mixing with an aqueous sodium aluminate composition and an aqueous solution of the template compound. This mixture is then converted under autogeneous pressure, the product is dried and then calcined. The pentasil type zeolites can be used in the conversion of methanol into hydrocarbons.

1 Claim, No Drawings

PROCESS FOR PREPARING A PENTASIL ZEOLITE

The present invention relates to templating compositions represented by the structural formula:

$(HO-C_2H_4)_3N^+-(CH_2)_n-N^+(C_2H_4-OH)_3 2Br^-$ the method for preparation thereof and utilization for the fabrication of zeolites of the pentasil type. Further, the present invention relates to the preparation of zeolites of the pentasil type, to zeolites of the pentasil type as well as the utilization thereof for the conversion of methanol into hydrocarbons.

Zeolites of the pentasil type are known. These are described by Doelle et al. in the Journal of Catalysis 71, pp. 27–40 (1981). Zeolites, in general, are described in Kirk-Othmer, Encyclopedia of Chemical Technology, 3rd Edition, Vol. 15, pp. 638–669.

In European Patent Specification No. 42 226, compounds of the following formula are described:

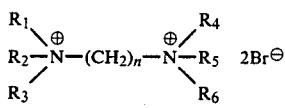

wherein n is 3 to 12, $R_1$ to $R_6$ can be the same or different and are alkyl or hydroxyalkyl groups containing 1 to 8 carbon atoms and wherein from 1 to 5 of the groups $R_1$ to $R_6$ can be hydrogen atoms.

Zeolites of the type EU-1 can be prepared with these compositions.

Zeolite EU-1 is not a zeolite of the pentasil type.

French Pat. No. 1,355,982 discloses compounds of the formula:

$(HO-C_2H_4)_3N^{\oplus}-(CH_2)_6-N^{\oplus}(C_2H_4-OH)_3 2Br^{\ominus}$ and $(HO-CH_2H_4)_3N^{\oplus}-(CH_2)_2-N^{\oplus}(C_2H_4-OH)_3 2Br^{\ominus}$.

Unfortunately, a zeolite of the pentasil type cannot be prepared utilizing these known compounds.

It is an object of the present invention to provide compounds having the formula:

$(HOC_2H_4)_3N^{\oplus}-(CH_2)_n-N^{\oplus}(C_2H_4-OH)_3 2Br^{\ominus}$ wherein n is 3, 4, or 5. These compounds will be referred to in the following by the art recognized expression "templating" compounds.

A further object of the present invention is to provide a method for the preparation of compounds of the formula:

$(HO-C_2H_4)_3N^{\oplus}-(CH_2)_n-N^{\oplus}(C_2H_4-OH)_3 2Br^{\ominus}$ wherein n equals 3, 4 or 5 which comprises reacting triethanolamine with α,ω dibromoalkanes containing 3, 4 or 5 carbon atoms, optionally in the presence of a solvent and then subsequently recovering the reaction product according to known methods.

In an advantageous embodiment of the invention, the triethanolamine as well as α,ω dibromoalkane compound can be dissolved together in a solvent and can be reacted together at the boiling point of the solvent to accomplish the desired reaction. In particular, the reaction can then be carried through with reflux conditions utilizing suitable apparatus.

As solvents, there may be used aliphatic alcohols such as, for example, ethanol, methanol, propanol and/or isomers thereof. For purposes of the invention, it is an essential condition that the solvent used in the reaction must be able to dissolve the reactants and function as a polar solvent for the duration of the reaction.

In accordance with another embodiment of the invention, the reaction between the triethanolamine and the α,ω dibromoalkane can be conducted in the absence of a solvent by charging the reactor with the triethanolamine and then adding the α,ω dibromoalkane thereto, advantageously in a stoichiometric amount, at an elevated reaction temperature, preferably between 100° and 115° C., not greater than 120° C. and wherein the α,ω dibromoalkane is added in a dropwise manner to the triethanolamine.

It is further object of the present invention to provide a method for the utilization of compounds of the formula:

$(HO-C_2H_4)_3N^{\oplus}-(CH_2)_n-N^{\oplus}(C_2H_4-OH)_3 2Br^{\ominus}$ wherein n equals 3, 4 or 5 for the preparation of zeolites of the pentasil type.

In accordance with the present invention, the zeolite of the pentasil type is characterized by a compositional formulation that is represented by:

$(0.4-0.7)Na_2O/(0.3-0.6)Q_2O/Al_2O_3/(30-80)SiO_2/(4-10)H_2O$ and an X-ray diffraction pattern which is set forth below:

| d Å | I/Io |
|---|---|
| 11.0 ± 0.2 | 30–70 |
| 10.0 ± 0.2 | 30–80 |
| 4.4 ± 0.1 | 10–20 |
| 4.3 ± 0.1 | 10–20 |
| 3.85 ± 0.05 | 100 |
| 3.74 ± 0.05 | 40–65 |
| 3.66 ± 0.05 | 20–40 |
| 3.43 ± 0.03 | 15–25 |
| 2.01 ± 0.02 | 5–15 |
| 1.99 ± 0.02 | 5–15 |

The zeolite of the present invention of the pentasil types is prepared in accordance with a further object of the present invention by first of all suspending a precipitated silica in water and then charging that suspension to a solution of sodium aluminate and sodium hydroxide in water. There is then also added a solution of:

$(HO-C_2H_4)_3N^{\oplus}-(CH_2)_n-N^{\oplus}(C_2H_4-OH)_3 2Br^{\ominus}$ wherein n equals 3, 4 or 5, in water, to provide a reaction mixture with a formulation: (1.0–4.0) templating compound: (5–10)Na₂O:Al₂O₃:(30–90)SiO₂:(900–3000)H₂O.

This aqueous reaction mixture is then treated under pressure at a temperature in the range of 100° to 180° C. within a time period of about 1 to 20 days. The reaction vessel is generally an autoclave operated under autogeneous pressure. The product is then isolated and then dried and then calcined at a temperature in the range of 300° to 600° C.

Any suitable precipitated silica can be used such as those described in Ullmann's Encyclopedia of Chemical Technology, 4th Edition, Vol. 21, pp. 465–467 which is relied on and incorporated by reference herein.

The concentration of the sodium aluminate and hydroxide solutions is not narrowly critical. A suitable concentration for the reaction mixture is achieved by the expedient of adding water. Likewise, the sequence of mixing of the components may be varied as desired. Equipment of any conventional type can be used for purposes of the invention. A mixing vessel with an impellor stirrer can suitably be used. The temperature of mixing lies between room temperature and the boiling point of the solution.

In accordance with the present invention, it has been found that the zeolite of the pentasil type can be utilized as a catalyst in the conversion of methanol to hydrocarbon materials.

The following examples illustrate the invention in further detail and are not intended to be limiting thereof in any way.

EXAMPLE 1

To 800 g of triethanolamine there is added in a dropwise manner 615 g 1,5 dibromopentane at a temperature of 110° C. under such conditions that the temperature does not rise above 120° C. Thereafter, the composition is stirred for 8 hours at a temperature of 110° C. Subsequently, there is added 1.5 liters of water. The high viscosity product is completely water soluble. The aqueous solution can be directly used for the preparation of zeolite. The analysis showed a 100% conversion.

EXAMPLE 2

577 g 1,4 dibromobutane is added dropwise to 800 g triethanolamine at 110° C. and the temperature is not permitted to exceed 120° C. The composition is then stirred for 8 hours at a temperature of 110° C. Subsequently, there is added 1.5 liters of water to the mixture. The high viscosity product resulting therefrom is completely water soluble. The aqueous solution can be directly utilized for the preparation of zeolite. The analysis showed a 100% conversion.

EXAMPLE 3

To 800 g triethanolamine there is added 540 g 1,3 dibromopropane in a dropwise manner at a temperature of 110° C., being careful not to exceed 120° C. Thereafter, the mixture is stirred for 8 hours at a temperature of 110° C. Subsequently, 1.5 liters of water is added to the composition. The high viscosity product is completely water soluble. The aqueous solution can be directly used for the preparation of zeolites. The analysis showed a 100% conversion.

EXAMPLE 4

To 800 g triethanolamine there is added 652 g 1,6 dibromohexane in a dropwise manner at a temperature of 110° C., being careful that the temperature of 120° C. is not exceeded. Thereafter, the mixture is stirred for a period of 8 hours at a 110° C. Subsequently, there is added 1.5 liters of water to the mixture. The resulting high viscosity product is completely water soluble. The aqueous solution can be directly used for the preparation of zeolites. The analysis showed a 100% conversion.

EXAMPLE 5

200 g triethanolamine and 150 g 1,5 dibromopentane are dissolved in 1 liter of ethanol and then heated under reflux for 48 hours. The separated precipitate is filtered off and is washed with ethanol. There is obtained 250 g of the product (=72.5%).

EXAMPLE 6

A suspension of 100 g precipitated silica in 700 ml water is added to a solution of 5 g sodium aluminate and 10 g sodium hydroxide in 75 ml water. To that composition, there is added 60 g of the aqueous solution which is obtained in accordance with Example 2. This reaction mixture which has a composition corresponding to the formulation: 2.3 templating composition according to Example 2: $6.4Na_2O:1Al_2O_3:60SiO_2:1800H_2O$ is then stirred in an autoclave at 160° C. under autogeneous pressure for 5 days. After cooling off of the product, it is then filtered, dried and then calcined at 550° C. for 5 hours. The X-ray diffraction pattern shows the characteristic points of a zeolite of the pentasil type.

The analysis of the isolated uncalcined product (with included cation) is shown as follows:
0.91% $Na_2O$
3.30% $Al_2O_3$
87.7% $SiO_2$
8.0% (1100° C.) ignition loss
3.33% C=6.01% cation.

The zeolite has the following stoichiometric composition:

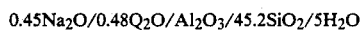

$0.45Na_2O/0.48Q_2O/Al_2O_3/45.2SiO_2/5H_2O$ wherein Q is a cation for charge equalization to $Al_2O_3$.

X-ray diffraction pattern:

| d Å | I/Io |
| --- | --- |
| 11.14 | 40 |
| 9.99 | 30 |
| 4.42 | 13 |
| 4.32 | 13 |
| 3.86 | 100 |
| 3.74 | 46 |
| 3.67 | 27 |
| 3.46 | 16 |
| 2.01 | 7 |
| 1.99 | 7 |

The analysis of the calcined product is as follows:
0.93% $Na_2O$
3.37% $Al_2O_3$
89.54% $SiO_2$
3.5% ignition loss
surface area 430 m²/g

EXAMPLE 7

A suspension of 300 g of precipitated silica in 2 liters of water is added to a solution of 30 g of sodium aluminate and 45 g sodium hydroxide in 300 ml water. To that, there is then added 198 g of the aqueous solution which is obtained in accordance with Example 3. This reaction mixture which has the compositional characteristics 1.3 templating compound according to Example 3: $5.1Na_2O:1Al_2O_3:31SiO_2:920H_2O$ is then stirred in an autoclave at 160° C. under its own pressure for 5 days.

After cooling off, the product is then filtered, dried and then calcined at 550° C. for 5 hours. The precipitated silica is identified as Degussa Product VN3 as described in Ullmann's Encyclopedia of Chemical Technology, 4th Edition, Vol. 21, page 467, Table 12. The X-ray diffraction pattern shows the characteristic features of a zeolite of the pentasil type.

The analysis was as follows:
1.77% $Na_2O$
4.69% $Al_2O_3$
82.4% $SiO_2$
11.0% ignition loss (1100° C.)
2.63% C The compositional formula was as follows:

$$0.62Na_2O/0.32Q_2O/Al_2O_3/30.0SiO_2/4.5H_2O$$

wherein Q is a cation for the charge equalization of $Al_2O_3$.

The X-ray diffraction pattern is shown below:

| d Å | I/Io |
| --- | --- |
| 11.05 | 50 |
| 9.99 | 42 |
| 4.42 | 15 |
| 4.32 | 13 |
| 3.83 | 100 |
| 3.74 | 55 |
| 3.67 | 35 |
| 3.45 | 18 |
| 2.01 | 9 |
| 1.99 | 8 |

EXAMPLE 8

A suspension of 300 g of precipitated silica in 2 liters of water is added to a solution of 107 g sodium aluminate and 35 g sodium hydroxide in 300 ml water. To that, there is then added 182 g of the aqueous solution which is obtained in accordance with Example 1. This reaction mixture which has a compositional characteristic represented as: 3.2 templating compound according to Example 1: $9.5Na_2O:1Al_2O_3:85SiO_2:2550H_2O$ is then stirred in an autoclave at 160° C. under its own pressure for 15 days. After cooling, the product is then filtered off, dried and calcined at 550° C. for 5 hours. The X-ray diffraction pattern shows the characteristic feature of a zeolite of the pentasil type.

The analysis of the resulting product is shown below:
0.60% $Na_2O$
1.93% $Al_2O_3$
89.1% $SiO_2$
8.3% ignition loss (1100° C.)
2.24% C The summary formula is shown below:

$$0.51Na_2O/0.58Q_2O/Al_2O_3/78.3SiO_2/7.3H_2O$$

wherein Q is a cation for charge equalization of $Al_2O_3$.
The X-ray diffraction pattern is shown below:

| d Å | I/Io |
| --- | --- |
| 10.95 | 35 |
| 9.99 | 30 |
| 4.43 | 12 |
| 4.35 | 10 |
| 3.84 | 100 |
| 3.73 | 62 |
| 3.66 | 25 |
| 3.40 | 22 |
| 2.01 | 5 |
| 1.99 | 6 |

EXAMPLE 9

A suspension of 200 g precipitated silica in 1.5 liter water is added to a solution of 10 g sodium aluminate and 20 g sodium hydroxide in 50 ml water. To that there is then added 124 g of the aqueous solution which is prepared in accordance with Example 1. The resulting reaction mixture which has a compositional formulation is: 2.3 templating compound according to Example 1: $6.4Na_2O:1Al_2O_3:60SiO_2:1800H_2O$ is then stirred in an autoclave at 140° C. under its own pressure for 8 days. After cooling, the product is then filtered, dried and calcined for 5 hours at 550° C. The X-ray diffraction pattern shows the characteristic features of zeolites of the pentasil type.

The analysis of the resulting product is shown below:
0.93% $Na_2O$
2.93% $Al_2O_3$
85.8% $SiO_2$
10.4% ignition loss (1100° C.)
2.29% C The summary formula is as follows:

$$0.52Na_2O/0.39Q_2O/Al_2O_3/49.7SiO_2/8.6H_2O$$

wherein Q is a cation for charge equalization of $Al_2O_3$.
The X-ray diffraction pattern is shown below:

| d Å | I/Io |
| --- | --- |
| 11.12 | 70 |
| 10.02 | 75 |
| 4.45 | 11 |
| 4.33 | 10 |
| 3.86 | 100 |
| 3.75 | 58 |
| 3.64 | 20 |
| 3.43 | 20 |
| 2.01 | 12 |
| 1.99 | 10 |

EXAMPLE 10 (COMPARATIVE EXAMPLE)

A suspension of 100 g precipitated silica in 750 ml water is added to a solution of 5 g sodium aluminate and 10 g sodium hydroxide in 25 liters of water. Then 90 g of a 50% solution of the templating compound:

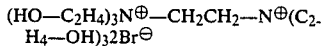

in water is added thereto. This reaction mixture which has a composition 2.3 templating compound: $6.4Na_2O:1Al_2O_3:60SiO_2:1800H_2O$ is then introduced into an autoclave and stirred at 160° C. under its own pressure for 5 days. After cooling, the product is then filtered off, dried and calcined at 550° C. for 5 hours. The X-ray diffraction spectrum shows no lines, thereby indicating an amorphous product.

EXAMPLE 11

The zeolite of the pentasil type which is prepared in accordance with Example 8 is then converted to a catalytically active acidic form by stirring the sodium form for 2 hours at 80° C. in an aqueous solution containing 2N $H_2SO_4$, filtering off the product and then drying at 120° C.

The resulting product is characterized by the following analysis: zeolite in the active hydrogen form:
- 0.01% $Na_2O$
- 3.06% $Al_2O_3$
- 93.0% $SiO_2$
- 3.9% ignition loss (1100° C.)

Summary formula:

$$0.005Na_2O/Al_2O_3/51.5SiO_2/7.2H_2O$$

The zeolite obtained thereby is then shaped by taking the zeolite powder and mixing with a silica sol (LUDOX HS 40) utilizing 0.7 ml of the silica sol per gram of zeolite to form a mass, and then pressing the mass through a sieve with a sieve opening of 1 mm, calcining at 400° C. for 4 hours and then selecting the sieve fraction 0.5 to 1.5 mm for conversion of the methanol.

EXAMPLE 12

The shaped zeolite according to Example 11 was then used in the conversion of methanol into a hydrocarbon material. In accordance with the procedure, the following process parameters are utilized:

| | |
|---|---|
| Temperature | 375° C. |
| Pressure | 5 bar |
| Methanol Partial Pressure | 2.2 bar |
| WHSV (Reactant steam velocity) | 2.9 per hour |

The product exhibits the following composition in accordance with weight percent:

| | |
|---|---|
| Methane | 1.6% |
| $C_2$-hydrocarbons | 6.7% |
| $C_3$-hydrocarbons | 14.7% |
| $C_4$-hydrocarbons | 20.2% |
| $C_5{}^+$-hydrocarbons | 56.8% of which 54% are aromatics |

Further variations and modifications of the present invention will become apparent to those skilled in the art from the foregoing description thereof. Such modifications and variations are intended to be encompassed by the claims appended hereto.

We claim:

1. A method for the preparation of a zeolite of the pentasil type which is represented by the formula:

(0.4–0.2)$Na_2O$/(0.3–0.6)$Q_2O$/$Al_2O_3$/(30–80)$SiO_2$/(4–10)$H_2O$ wherein Q is an organic cation and by the x-ray diffraction pattern:

| d (Å) | I/Io |
|---|---|
| 11.0 ± 0.2 | 30–70 |
| 10.0 ± 0.2 | 30–80 |
| 4.4 ± 0.1 | 10–20 |
| 4.3 ± 0.1 | 10–20 |
| 3.85 ± 0.05 | 100 |
| 3.74 ± 0.05 | 40–65 |
| 3.66 ± 0.05 | 20–40 |
| 3.43 ± 0.03 | 15–25 |
| 2.01 ± 0.02 | 5–15 |
| 1.99 ± 0.02 | 5–15 | comprising suspending precipitated silica in water and adding thereto an aqueous solution of sodium aluminate and sodium hydroxide in water, providing a solution of a templating compound represented by the formula:

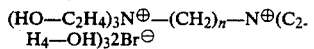

(HO—$C_2H_4$)$_3$N$^\oplus$—(CH$_2$)$_n$—N$^\oplus$($C_2H_4$—OH)$_3$2Br$^\ominus$ wherein n equals 3, 4, or 5 in water, and combining said solutions for the preparation of a reaction mixture with a composition (1.0–4.0) templating compound: (5–10)$Na_2O$:$Al_2O_3$:(30–90)$SiO_2$:(900–3000)$H_2O$, subjecting the reaction mixture to autogeneous pressure at a temperature range of 100° to 180° C. within a time period of 1 to 20 days, isolating the product so obtained, drying and then calcining at a temperature ranging from 300° to 600° C.

* * * * *